US007455989B2

(12) United States Patent
Geiger (10) Patent No.: US 7,455,989 B2
(45) Date of Patent: Nov. 25, 2008

(54) AKAP84 AND ITS USE FOR VISUALIZATION OF BIOLOGICAL STRUCTURES

(75) Inventor: Benjamin Geiger, Rehovot (IL)

(73) Assignee: Yeda Research and Development Co. Ltd., Rechovot (IL)

( * ) Notice: Subject to any disclaimer, the term of this patent is extended or adjusted under 35 U.S.C. 154(b) by 92 days.

(21) Appl. No.: 10/524,275

(22) PCT Filed: Aug. 17, 2003

(86) PCT No.: PCT/IL03/00680

§ 371 (c)(1),
(2), (4) Date: Feb. 11, 2005

(87) PCT Pub. No.: WO2004/018505

PCT Pub. Date: Mar. 4, 2004

(65) Prior Publication Data

US 2006/0166186 A1     Jul. 27, 2006

Related U.S. Application Data

(60) Provisional application No. 60/404,386, filed on Aug. 20, 2002.

(51) Int. Cl.
C12P 21/06 (2006.01)
(52) U.S. Cl. .................................. 435/69.1
(58) Field of Classification Search ............ 435/69.1
See application file for complete search history.

(56) References Cited

U.S. PATENT DOCUMENTS

2002/0025536 A1   2/2002   Gyuris et al.

FOREIGN PATENT DOCUMENTS

| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 97/08553 | 6/1997 |

OTHER PUBLICATIONS

Prufer et al. 2000; Dimerization with retinoid X receptors promotes nuclear localization and subnuclear targeting of vitamin D receptors. J. Biol. Chem. 275 (52): 41114-41123.*
Day et al. Sep. 2001; Fluorescence resonance energy transfer microscopy of localized protein interactions in the living cell nucleus. Methods 25: 4-18.*
Xu et al. 1998; A bioluminescence resonance energy transfer (BRET) system: Application to interacting circadian clock proteins. Proc Natl Acad Sci U S A. Jan. 5, 1999; 96(1): 151-156.*
Furusawa Makoto et al. "AMY-1, A C-Myc-Binding Protein, Is Localized in the Mitochondria of Sperm by Association With S-AKAP84, An Anchor Protein of cAMP-Dependent Protein Kinase", The Journal of Biological Chemistry, 276(39):36647-36651, 2001.
Alam et al. "Germ Line Transmission and Expression of A LacZ Containing Transgene in Tilapia (Oreochromis Niloticus)", Transgenic Research, 5: 87-95, 1996.
Jockusch et al. "The Molecular Architecture of Focal Adhesions", Annual Reviews of Cell Development Biology, 11: 379-416, 1995.
Janmey "Phosphoinositides and Calcium as Regulators of Cellular Actin Assembly and Disassembly", Annual Reviews of Physiology, 56: 169-191, 1994.
Barras III "Assembly of Combinatorial Antibody Libraries on Phage Surfaces: The Gene III Site", Proc. Natl. Acad. Sci. USA, 88: 7978-7982, 1991.
Bilang et al. "The 3'-Terminal Region of the Hygromycin-B-Resistance Gene Is Important for Its Activity in *Escherichia coli* and *Nicotiana tabacum*", Gene, 100: 247-250, 1991.
Brinkly "A Brief Survey of Methods for Preparing Protein Conjugates With Dyes, Haptens, and Cross-Linking Reagents", Bioconjugate Chemistry, 3: 2-13, 1992.
Brousseau et al. "Hyperalphalipoproteinemia in Human Lecithin Cholesterol Acyltransferase Transgenic Rabbits", The Journal of Clinical Investigation, 97(8): 1844-1851, 1996.
Geiger et al. "The Cytoplasmic Domain of Adherens-Type Junctions", Cell Motility and the Cytoskeleton, 20: 1-6, 1991.
Clackson et al. "Making Antibody Fragments Using Phage Display Libraries", Nature, 352: 624-628, 1991.
Cozzi et al. "Longitudinal Analysis of the Expression of Human Decay Accelerating Factor (HDAF) on Lymphocytes, in the Plasma, and in the Skin Biopsies of Transgeinc Pigs", Xenotransplantation, 3: 128-133, 1996.
Tsukita et al. "Molecular Linkage Between Cadherins and Actin Filaments in Cell-Cell Adherens Junctions", Current Opinion in Cell Biology, 4: 834-839, 1992.
Damak et al. "Improved Wool Production in Transgenic Sheep Expressing Insulin-Like Growth Factor 1", Bio/Technology, 14: 185-188, 1996.
Danon et al. "Light Regulated Translational Activators: Identification of Chloroplast Gene Specific mRNA Binding Proteins", The EMBO Journal, 10(13): 3993-4001, 1991.
De Block et al. "Transformation of *Brassica napus* and *Brassica oleracea* Using *Agrobacterium tumefaciens* and the Expression of the Bar and Neo Genes in the Transgenic Plants", Plant Physiology, 91: 694-701, 1989.
Deng et al. "Selection of Antibody Single-Chain Variable Fragments With Improved Carbohydrate Binding by Phage Display", The Journal of Biological Chemistry, 269(13): 9533-9538, 1994.
Dower "Electroporation of Bacteria: A General Approach to Genetic Transformation", Genetic Engineering, Principles and Methods, 12: 275-296, 1990.

(Continued)

*Primary Examiner*—Karen Cochrane Carlson (57) ABSTRACT

A polynucleotide encoding a chimeric polypeptide is provided. The chimeric polypeptide includes (a) a first polypeptide region being capable of specifically binding at least one detectable molecule; and (b) a second polypeptide region being capable of specifically binding a biological component or macromolecule or targeting a cellular compartment. Methods utilizing the polynucleotide or the chimeric polypeptide for highlighting a cell compartment, a biological component or macromolecule are also provided.

16 Claims, 1 Drawing Sheet

OTHER PUBLICATIONS

Duncker et al. "Expression of A Cystine-Rich Fish Antifreeze in Transgenic Drosophila Melanogaster", Transgenic Research, 5: 49-55, 1996.

Duncker et al. "Antifreeze Protein Does Not Confer Cold Tolerance to Transgenic Drosophila Melanogaster", Cryobiology, 32: 521-527, 1995.

Dziadek "Transgenic Animals: How They Are Made and Their Role in Animal Production and Research", Australian Veterinary Journal, 73(5): 182-187, 1996.

Faux et al. "Molecular Glue: Kinase Anchoring and Scaffold Proteins", Cell, 85: 9-12, 1996.

Fuchs et al. "Targeting Recombinant Antibodies to the Surface of *Escherichia coli*: Fusion to A Peptidoglycan Associated Lipoprotein", Bio/Technology, 9: 1370-1372, 1991.

Garrard et al. "Fab Assembly and Enrichment in A Monovalent Phage Display System", Bio/Technology, 9: 1373-1377, 1991.

Garrard et al. "Selection of An Anti-IGF-1 Fab From A Fab Phage Library Created by Mutagenesis of Multiple CDR Loops", Gene, 128: 103-109, 1993.

Glatz et al. "Cellular Fatty Acid-Binding Proteins: Their Function and Physiological Significance", Progressive Lipid Research, 35(3): 243-282, 1996.

Gram et al "In Vitro Selection and Affinity Maturation of Antibodies From A Naive Combinatorial Immunoglobulin Library", Proc. Natl. Acad. Sci. USA, 89: 3576-3580, 1992.

Griffiths et al. "Human Anti-Self Antibodies With High Specificity From Phage Display Libraries", The EMBO Journal, 12(2): 725-734, 1993.

Guerche et al. "Direct Gene Transfer by Electroporation in *Brassica napus*", Plant Science, 52: 111-116, 1987.

Hanahan et al. "Plasmid Transformation of *Escherichia coli* and Other Bacteria", Methods in Enzymology, 204: 63-113, 1991.

Hawkins et al. "Selection of Phage Antibodies by Binding Affinity. Mimicking Affinity Maturation", Journal of Molecular Biology, 226: 889-896, 1992.

Hawkins et al. "The Contribution of Contact and Non-Contact Residues of Antibody in the Affinity of Binding to Antigen. The Interaction of Mutant D1.3 Antibodies With Lysozyme", Journal of Molecular Biology, 234: 958-964, 1993.

Hay et al. "Bacteriophage Cloning and *Escherichia coli* Expression of A Human IgM Fab", Human Antibody Hybridomas, 3: 81-85, 1992.

Hoogenboom et al. "Multi-Subunit Proteins on the Surface of Filamentous Phage: Methodologies for Displaying Antibody (Fab) Heavy and Light Chains", Nucleic Acids Research, 19(15): 4133-4137, 1991.

Horsch et al. "A Simple and General Method for Transferring Genes Into Plants", Science, 277: 1229-1231, 1985.

Howell et al. "Cloned Cauliflower Mosaic Virus DNA Infects Turnips (*Brassica rapa*)", Science, 208: 1265-1267, 1980.

Huse et al. "Generation of A Large Combinatorial Library of the Immunoglobulin Repertoire in Phage Lambda", Science, 246(4935): 1275-1281, 1989.

Knudsen et al. "Interction of α-Actinin With the Cadherin/Catenin Cell-Cell Adhesion Complex Via α-Catenin", The Journal of Cell Biology, 130(1): 67-77, 1995.

Itoh et al. "Involvement of ZO-1 in Cadherin-Based Cell Adhesion Through Its Direct Binding to a Catenin and Actin Filaments", The Journal of Cell Biology, 138(1): 181-192, 1997.

Kang et al. "Linkage of Recognition and Replication Functions by Assembling Combinatorial Antibody Fab Libraries Along Phage Surfaces", Proc. Natl. Acad. Sci. USA, 88: 4363-4366, 1991.

Keller et al. "In Vivo Particle-Mediated Cytokine Gene Transfer Into Canine Oral Mucosa and Epidermis", Cancer Gene Therapy, 3(3): 186-191, 1996.

Kim et al. "Neuron-Specific Expression of A Chicken Gicerin cDNA in Transient Transgenic Zebrafish", Neurochemical Research, 21(2): 231-237, 1996.

Klein et al. "High-Velocity Microprojectiles for Delivering Nucleic Acids Into Living Cells", Nature, 327:70-73, 1987.

Kroshus et al. "Expression of Human CD59 in Transgenic Pig Organs Enhances Organ Survival in An Ex Vivo Xenogeneic Perfusion Model", Transplantation, 61(10): 1513-1521, 1996.

Lai et al. "An Extended Family of Protein-Tyrosine Kinase Genes Differentially Expressed in the Vertebrate Nervous System", Neuron, 6: 691-704, 1991.

Lin et al. "Characterization of S-AKAP84, A Novel Developmentally Regulated A Kinase Anchor Protein of Male Germ Cells", The Journal of Biological Chemistry, 270(46): 27804-27811, 1995.

Lo "Animal Models of Human Disease. Transgenic and Knockout Models of autoimmunity: Building A Better Disease?", Clinical Immunology and Immunobiology, 79(2): 96-104, 1996.

Lorimer et al. "Recombinant Immunotoxins Specific for A Mutant Epidermal Growth Factor Receptor: Targeting With A Single Chain Antibody Variable Domain Isolated by Phage Display", Proc. Natl. Acad. Sci. USA, 93: 14815-14820, 1996.

McCafferty et al. "Phage Antibodies: Filamentous Phage Displaying Antibody Variable Domains", Nature, 348: 552-554, 1990.

Mitchell et al. "Transgene Expression in the Rhesus Cervix Mediated by An Adenovirus Expressing β-Galactosidase", American Journal of Obstetical Gynecology, 174: 1094-1101, 1996.

Ndubuka et al. "Expression of A Kinase Anchor Protein 75 Depletes Type II cAMP-Dependent Protein Kinases From the Cytoplasm and Sequesters the Kinases in A Particulate Pool", The Journal of Biological Chemistry, 268(11): 7621-7624, 1993.

Neuhaus et al. "Transgenic Rapeseed Plants Obtained by the Microinjection of DNA Into Microspore-Derived Embryoids", Theoretical Applied Genetics, 75: 30-36, 1987.

Rimm et al. "α1 (E)-Catenin Is An Actin-Binding Protein Mediating the Attachment of F-Actin to the Membrane Adhesion Complex", Proc. Natl. Acad. Sci. USA, 92: 8813-8817, 1995.

Rexroad Jr. et al. "Evaluation of Co-Culture as A Method for Selecting Viable Microinjected Sheep Embryos for Transfer", Animal Biotechnology, 1(1): 1-10, 1990.

Rubin "A Kinase Anchor Proteins and the Intracellular Targeting of Signals Carried by Cyclic AMP", Biochimica et Biophysica Acta, 1224: 467-479, 1994.

Sastry et al. "Cloning of the Immunological Repertoire in *Escherichia coli* for Generation of Monoclonal Catalytic Antibodies: Construction of Heavy Chain Variable Region-Specific cDNA Library", Proc. Natl. Acad. Sci. USA, 86: 5728-5732, 1989.

Mittelsten Scheid et al. "Reversible Inactivation of A Transgene in Arabidopsis Thaliana", Molecular Gene & Genetics, 228: 104-112, 1991.

Scott et al. "Localization of A-Kinase Through Anchoring Proteins", Molecular Endocrinology, 8(1): 5-11, 1994.

Shanahan et al. "Regulation of Expression of A Sheep Metallothionein 1A-Sheep Growth Hormone Fusion Gene in Transgenic Mice", Molecular and Cellular Biology, 9(12): 5473-5479, 1989.

Shen et al. "Transgenic Rabbits With the Integrated Human 15-Lipoxygenase Gene Driven by A Lysozyme Promoter: Macrophage-Specific Expression and Variable Positional Specificity of the Transgenic Enzyme", The FASEB Journal, 9: 1623-1631, 1995.

Simoens et al. "Genetic Engineering in Plants", Human Reproduction Update, 1(6): 523-542, 1995.

Wagner et al. "The Renin-Angiotensin System in Transgenic Rats", Pediatric Nephrology, 10: 108-112, 1996.

Wall et al. "Synthesis and Secretion of the Mouse Whey Acidic Protein in Transgenic Sheep", Transgenic Research, 5: 67-72, 1996.

Wall "Transgenic Livestock: Progress and Prospects for the Future", Theriogenology, 45: 57-68, 1996.

Whitehorn et al. "A Generic Method for Expression and Use of 'Tagged' Soluble Versions of cell Surface Receptors", Bio/Technology, 13: 1215-1219, 1995.

Wilks "Two Putative Protein-Tyrosine Kinases Indentified by Application of the Polymerase Chain Reaction", Proc. Natl. Acad. Sci. USA, 86: 1603-1607, 1989.

Zebedee et al. "Human Combinatorial Antibody Libraries to Hepatitis B Surface Antigen", Proc. Natl. Acad. Sci. USA, 89: 3175-3179, 1992.

* cited by examiner

AKAP84 AND ITS USE FOR VISUALIZATION OF BIOLOGICAL STRUCTURES

RELATED PATENT APPLICATION

This application is a National Phase Application of PCT/IL03/00680 having International Filing Date of 17 Aug. 2003, which claims priority from U.S. Provisional Patent Application No. 60/404,386 filed 20 Aug. 2002.

FIELD AND BACKGROUND OF THE INVENTION

The present invention relates to novel methods of staining cell compartments, biological components or macromolecules. Specifically, the present invention relates to chimeric polypeptides and nucleic acid constructs encoding same which can be used to selectively stain or highlight cell compartments, biological components or macromolecules.

Various diagnostic and research techniques rely upon specific or non-specific biological staining typically effected using molecules which are either applied to cells or tissues (dyes) or expressed in cells or tissues (reporter genes).

Dyes are typically used for the purpose of highlighting specific cells within a tissue or specific cell components within a cell. Certain dyes, referred to here as vital stains, are capable of staining cells without killing them. Yet, vital stains are not sufficiently selective for highlighting specific cellular components such as specific receptors, cellular organelles or cytoskeletal structures.

Reporter genes, which encode readily assayed proteins, are utilized for marking specific cell components as well as to track expression of exogenous genes in cells. When expressed, fused to a desired partner protein, such as a structural protein, a visual signal is generated which specifically indicates the intracellular fate and position of the partner protein. Among the commonly used reporter genes are those encoding for β-galactosidase, β-glucuronidase, luciferase, and Green Fluorescent Protein (GFP).

GFP and variants thereof (e.g., CFP, YFP) are generally preferred in cases where cellular functions are to be kept unperturbed or when tracking the fate of an expressed protein over a period of time is required. GFP autofluoresces, therefore its use does not require the addition of exogenous signal-producing substrates as required by reporter enzymes such as β-galactosidase, β-glucuronidase or luciferase.

Although the use of reporter gene constructs provides numerous benefits, their generated signal may be, at times, more difficult to detect as compared to fluorescent dyes and as such use of reporter genes is limited to cases where sensitivity or high resolution is not critical. In addition, such proteins often display a limited repertoire of fluorescence spectra.

The present invention provides a novel approach for highlighting specific cell compartments, biological components or macromolecules in a manner that does not disturb cell functions, is highly target selective, and sensitive.

SUMMARY OF THE INVENTION

According to the present invention there is provided a polynucleotide comprising a nucleic acid sequence encoding a chimeric polypeptide, the chimeric polypeptide including (a) a first polypeptide region being capable of specifically binding at least one detectable molecule; and (b) a second polypeptide region being capable of (i) specifically binding a biological component or macromolecule; or (ii) targeting into a specific cell compartment.

According to another aspect of the present invention there is provided a nucleic acid construct comprising the polynucleotide described above.

According to further features in preferred embodiments of the invention described below, the nucleic acid construct further includes a promoter being for directing expression of the polynucleotide.

According to still another aspect of the present invention there is provided a cell comprising the polynucleotide described above.

According to an additional aspect of the present invention there is provided a chimeric polypeptide comprising: (a) a first polypeptide region being capable of specifically binding at least one detectable molecule; and (b) a second polypeptide region being capable of (i) specifically binding a biological component or macromolecule; or (ii) targeting into a specific cell compartment.

According to still further features in the described preferred embodiments, the detectable molecule includes a signal generating moiety selected from the group consisting of a fluorogenic moiety, a chromogenic moiety, a light emitting moiety, a radioactive moiety and any moiety detectable via modalities such as X-ray, ultrasound, MRI and the like.

According to still further features in the described preferred embodiments, the fluorogenic moiety is selected from the group consisting of coumarins, xanthene dyes, fluoresceins, rhodols, rhodamines, resorufins, cyanine dyes, bimanes, acridines, isoindoles, dansyl dyes, aminophthalic hydrazides, luminol, aminophthalimides, aminonaphthalimides, aminobenzofurans, aminoquinolines, dicyanohydroquinones, europium and terbium complexes.

According to still further features in the described preferred embodiments, the first polypeptide region of the chimeric polypeptide includes an antigen binding region of an antibody.

According to still further features in the described preferred embodiments, the antigen binding region is an Fv region.

According to still further features in the described preferred embodiments, the antigen binding region is a single chain Fv.

According to another aspect of the present invention there is provided a method of highlighting a cell compartment, a biological component or macromolecule in an organism comprising (a) providing a chimeric polypeptide to the organism, the chimeric polypeptide including (i) a first polypeptide region being capable of specifically binding at least one detectable molecule; and (ii) a second polypeptide region being capable of specifically binding the biological component or macromolecule of the organism; or targeting into a specific cell compartment; and (b) exposing the organism to the detectable molecule under conditions suitable for binding of the detectable molecule to the first polypeptide region thereby highlighting the cell compartment biological component or macromolecule in the organism.

According to further features in preferred embodiments of this aspect of the invention described below the organism is selected from the group consisting of a virus, a bacterium, a protozoa, a fungus, a yeast, an algae, a plant and an animal.

According to an additional aspect of the present invention there is provided a method of identifying a phenotypic abnormality in a subject comprising (a) providing a chimeric polypeptide to the subject the chimeric polypeptide including (i) a first polypeptide region being capable of specifically binding at least one detectable molecule, and (ii) a second polypeptide region being capable of specifically binding a biological component or macromolecule being indicative of the phenotypic abnormality; and (b) exposing the subject to the detectable molecule under conditions suitable for binding of the detectable molecule to the first polypeptide region thereby highlighting the biological component or macromolecule and identifying the phenotypic abnormality in the subject.

According to further features in preferred embodiments of this aspect of the invention described below the subject is a plant or an animal.

According to still further features in the described preferred embodiments the subject is a human.

According to still further features in the described preferred embodiments the phenotypic abnormality is associated with a disease.

According to still further features in the described preferred embodiments the phenotypic abnormality is associated with cancer.

According to still further features in the described preferred embodiments the method further comprises the step of comparing a pattern or intensity of the highlighting in the subject to that of a normal subject.

According to an additional aspect of the present invention there is provided a method of identifying the presence of an infectious agent in a subject comprising (a) providing a chimeric polypeptide to the subject, the chimeric polypeptide including (i) a first polypeptide region being capable of specifically binding at least one detectable molecule; and (ii) a second polypeptide region being capable of specifically binding the infectious agent or targeting into the infectious agent; and (b) exposing the subject to the detectable molecule under conditions suitable for binding of the detectable molecule to the first polypeptide region thereby highlighting the infectious agent and identifying the presence thereof in the subject.

According to further features in preferred embodiments of this aspect of the invention described below the infectious agent is selected from the group consisting of a virus, a bacterium, a protozoa, a fungus, a yeast, an algae, a plant and an animal.

According to still further features in the described preferred embodiments, the step of exposing the organism or the subject to the detectable molecule is effected by administering the detectable molecule to the organism or the subject.

According to still further features in the described preferred embodiments, the step of providing the chimeric polypeptide to the organism or the subject is effected by expressing the chimeric polypeptide within the organism or the subject.

According to still further features in the described preferred embodiments there is an additional step of visualizing the detectable molecule.

According to still further features in the described preferred embodiments the step of visualizing is effected using a microscope.

According to still further features in the described preferred embodiments the microscope is equipped with a light source.

The present invention successfully addresses the shortcomings of the presently known configurations by providing polypeptides, nucleic acid constructs encoding same and methods using the polypeptides and nucleic acid constructs for biological staining that is highly specific, sensitive and can be widely applied.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of polypeptides and polynucleotides encoding same and methods of using such polynucleotides or polypeptides for highlighting or visualizing specific cell compartments, biological components or macromolecules, in vivo or in vitro. The methodology of the present invention provides a highlighting approach which does not disturb cellular functions or morphology, provides a high degree of accuracy and sensitivity and can be utilized for both research and diagnostic purposes.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention addresses the growing need to directly visualize specific cell compartments, biological components or macromolecules in situ and without disturbing the normal function of the organism. The current art of biological staining relies upon either vital stains or reporter genes. Vital stains are typically utilized for highlighting relatively large cellular constituents, such as the cell wall, protoplasm or vacuole, however, their molecular specificity is limited.

Reporter proteins, on the other hand, are highly specific since they can be expressed in a targeted manner. However, the signal generated from expressed reporter proteins in a cell is oftentimes too weak or absorbed in background for highlighting a specific cell compartment, biological component or macromolecule in situ.

The present invention provides a novel approach for highlighting whole cells, cell compartments, biological components or macromolecules thereof, which approach is both sensitive, non toxic, can be effected in situ or in vivo, and enabling the use of a variety of highlighting colors.

The present invention provides a chimeric polypeptide which is capable of binding a biological component (e.g., cell, or cell membrane) or a macromolecule (e.g., a receptor, or a binding protein), and a detectable molecule such as a fluorophore, such that when expressed in, or provided to, a cell exposed to the detectable molecule, the chimeric polypeptide of the present invention is designed capable of binding and localizing the detectable molecule to the cell, cell compartment or cell component thereby enabling visualization thereof.

Thus, according to one aspect of the present invention there is provided a chimeric polypeptide which is composed of two fused polypeptide regions: a first polypeptide region which is capable of specifically binding at least one detectable molecule, and a second polypeptide region which is capable of specifically targeting into a specific cell compartment and/or binding a biological component or macromolecule.

As used herein, the phrase "biological component" refers to any morphologically distinct entity within an organism including tissue, cell, cell nucleus, cytoskeletal fibers, cell wall, membrane, organelle and the like.

As used herein, the term "macromolecule" refers to a large molecule composed of smaller subunits. Examples of macromolecules include polypeptides, including proteins and glycoproteins, polynucleotides, polysaccharides, and lipids.

As used herein, the phrase "cell compartment" refers to a cellular or subcellular recognized structure. Examples of cell compartments include a mitochondrion, lysosome, vacoule, a nucleus, and an endoplasmic reticulum.

As used herein, the phrase "detectable molecule" refers to a molecule which can be directly or indirectly detected.

Examples of detectable molecules which can be used with the present invention include molecules which include a signal generating moiety such as a fluorogenic moiety, a chromogenic moiety, a light emitting moiety, a radioactive moiety or any moiety detectable via imaging modalities utilizing an X-ray, ultrasound or MRI imaging fields.

Detectable molecules suitable for use with the present invention can be obtained from a commercial supplier of chemicals (e.g., Sigma Chemicals). The detectable molecule is selected for use on a case by case basis based upon special needs or limitations of the user such as the required membrane permeability, binding affinity to non-target sites, signal spectrum of emission, or signal sensitivity (i.e., quantum yield). A detectable molecule may be selected from numerous traditional color-generating (chromogenic) vital stains such as orange G, neutral red, brilliant cresyl blue, toludine blue, chrysiodine or rhodamine B, trypan blue, ethidium bromide, ethidium homodimer or diethylene triamine. Preferably, fluorescing dyes (fluorophores) are selected due to their greater sensitivity and compatibility with powerful visualizing enabling technologies (e.g., fluorescent microscopy).

Hence, in a preferred embodiment of this aspect of the invention, the detectable molecule includes a signal generating fluorogenic moiety selected from the group consisting of coumarins and related fluorophores, xanthene fluorophores, fluoresceins, rhodols, rhodamines, resorufins, cyanine fluorophores, bimanes, acridines, isoindoles, dansyl fluorophores, aminophthalic hydrazides, luminol, aminophthalimides, aminonaphthalimides, aminobenzofurans, aminoquinolines, dicyanohydroquinones, europium and terbium complexes.

Several chimeric polypeptide configuration are envisioned by the present invention.

The first polypeptide region of the chimeric polypeptide of the present invention can include any peptide sequence capable of binding a detectable molecule.

Preferably, the first polypeptide region of the chimeric polypeptide includes an antigen binding region of an antibody such as an Fv region, most preferably a single chain Fv region.

The term "single chain Fv (scFv)" as used herein refers to a single chained polypeptide which includes the variable region of the light chain and the variable region of the heavy chain, or a portion thereof, linked by a suitable polypeptide linker.

Methods of generating antibody sequences capable of binding a detectable molecule such as a fluorophore, are well known in the art.

Initially, the detectable molecule is utilized to immunize a host animal. In cases where the detectable molecule is too small to elicit a good immune response in the host animal (i.e., a hapten), it is preferably conjugated (i.e., covalently coupled) to a larger molecule having the property of independently eliciting an immunological response in a host animal (i.e., a carrier). Suitable carriers include, but are not limited to, bovine serum albumin (BSA), bovine thyroglobulin (BT), keyhole limpet hemocyanin (KLH), ovalbumin (OA), and the like, the KLH is preferred. Methods of conjugation are well known to a person skilled in the art, such as methods described by Brinkley [Bioconjugate Chem. 3:2-13 (1992)], preferably using the procedure described in details by Sastry et al. [Proc. Natl. Acad. Sci. 86: 5728-5732 (1989)]. The preparation procedure can further include an adjuvant, such as Freund's complete or incomplete adjuvant, or similar immunostimulatory agent.

Following immunization, the spleens of the host animal are removed and poly A+ mRNA extracted therefrom is utilized to construct a phage display library [Kang, et al., (1991) Proc. Natl. Acad. Sci., U.S.A., 88:4363; Barbas, et al., (1991) Proc. Natl. Acad. Sci., U.S.A., 88:7978].

Generating and screening phage display libraries can be done using commercially available kits (e.g., Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display libraries can be found in, for example Ladner et al. U.S. Pat. No. 5,223,409; International Publication Nos. WO 92/18619; WO 91/17271, WO 92/20791; WO 92/15679; WO 93/01288; WO 92/01047; WO 92/09690; Fuchs et al. (1991) Bio/Technology 9:1370-1372; Hay et al. (1992) Hum Antibody Hybridomas 3:81-85; Huse et al. (1989) Science 246:1275-1281; Griffiths et al. (1993) EMBO J. 12:725-734; Hawkins et al. (1992) J Mol Biol 226:889-896; Clarkson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:41334137; Barbas et al. (1991) PNAS 88:7978-7982; and McCafferty et al. Nature (1990) 348:552-554.

Antibodies possessing desirable binding properties are selected by binding to immobilized antigen in a process called "panning." Phage bearing nonspecific antibodies are removed by washing, and then the bound phage are eluted and amplified by infection of *E. coli*. This approach has been applied to generate antibodies against many antigens, including: hepatitis B surface antigen [Zebedee et al., (1992) PNAS 89:3175-31795] polysaccharides [Deng, S., et al.,(1994) J. Biol. Chem. 269:9533-9538]; insulin-like growth factor 1 [Garrard, L. J., et al., (1993) Gene 128: 103-109]; 2-phenyloxazol-5-one and 4-hydroxy-5-iodo-3-nitro-phenacetyl-(NIP)-caproic acid [Hawkins, R. E., et al., (1993) J. Mol. Biol. 234: 958-964]. Further details on methods of producing scFv are described by Pluckthum [The Pharmacology of Monoclonal Antibodies, Vol 113: Rosenburg and Moors eds. Springer-Verlag, New York, pp. 269-315 (1994)].

Once a recombinant monoclonal antibody specific for the detectable molecule has been identified, the cDNA encoding the antibody can be recovered from the phage display package and isolated using standard molecular biology techniques. Once obtained, the antibody sequence is cloned into a recombinant expression vector using standard methods. The expression vector can encode an intracellular antibody in one of several different forms. Preferably, the vector encodes a single chain antibody (scFv).

The target specificity of the second polypeptide region of the chimeric protein is selected according to the intended purpose of the chimeric polypeptide of the present invention Thus, in cases where the chimeric polypeptide is utilized for membrane localization or anchoring of the detectable molecule, the second polypeptide region includes a polypeptide sequence which is selected capable of binding a cell membrane, or any part thereof.

In such cases, the second polypeptide region includes a membrane attachment domain such as that described in Table 2 of U.S. Pat. No. 5,891,432, a binding polypeptide derived from a cell adhesion molecule [Pigott and Power (1993) The adhesion Molecule facts Book San Diego: Academic Press, Inc.] or a binding polypeptide derived from a membrane anchor protein such as phosphatidylinositol-glycan (PI-G) [Whitehorn et al. (1995) Biotechnology 13:1215-1219], hipR (U.S. Pat. No. 5,968,769), human SDH Q-reductase (U.S. Pat. No. 5,985,638) or growth factor receptor [Wilks Proc. Natl. Acad. Sci. USA 36, 1603 (1989) and Lai et al. Neuron 6, 691 (1991)].

The second polypeptide region of the chimeric polypeptide can also be selected of a sequence capable of binding a specific receptor of a cell membrane. In such cases, the second polypeptide region can include a receptor-binding ligand sequence, see for example, U.S. Pat. No. 5,650,504.

In cases where specific organelles are to be targeted, the second polypeptide region of the chimeric protein is selected of a sequence capable of specifically binding a cell organelle, or any part thereof. For example, various isomers of protein kinase AII (PKAII) bind mitochondria, peroxisomes and a variety of cell types via a target specific attachment to protein kinase A anchor proteins (AKAPs) [Rubin, C. S. (1994) Biochem. Biophys. Acta 1224:467-479; Scott, J. D., and McCartney, S. (1994) Mol. Endocrinol. 8:5-11; Faux, M. and Scott, J. D. (1966) Cell 9-12].

Thus, the second polypeptide region can include organelle binding sequences of PKAII. One peptide sequence which can be used as the second polypeptide region encompasses the S-AKAP84 peptide which binds a specific site (RII) located in the cytoplasm adjacent to the mitochondrial surface. The isolation of cDNA encoding S-AKAP84, DNA sequence analysis, cloning and expression of S-AKAP84, are described by Chen et al. [J. Mol. Chem. 272:15247-15257 (1997)].

The sequence of the second polypeptide region of the chimeric polypeptide can also be selected capable of specifically binding a cell wall. Preferably it is selected capable of binding the cellulosic component of the cell wall. As such the second polypeptide can include a cellulose binding domain (CBD) or a derivative thereof. Detail of nucleic acids sequences encoding CBD are disclosed in U.S. Pat. Nos. 5,202,247; 5,137,819; 5,340,731; and 5,594,934.

The sequence of the second polypeptide region of the chimeric polypeptide can also be selected capable of specifically binding a macromolecule expressed within, displayed upon or secreted from, a cell. The macromolecule can be cell specific or it can be non-cell specific.

For example, the second polypeptide region can be selected capable of binding low density lipoprotein (U.S. Pat. No. 6,355,451), or a lipid. In the latter case, the second polypeptide region can include the lipid binding domain of lipid-binding proteins/fatty acid-binding proteins (FABPs) [described by Glatz, J. F., van der Vusse, G. J (1996) Cellular fatty acid-binding proteins: their function and physiological significance. *Prog. Lipid Res.* 35:243-282] as well as derivatives and analogs thereof.

The macromolecule can also be a polynucleotide. In such cases, the second polypeptide region can include a polynucleotide binding domain of any protein or polypeptide that binds with high affinity and specificity to DNA or RNA. Examples include polypeptides which bind the 5' UTR of the chloroplast encoded psbA mRNA [Danon and Mayfield, Embo J., 10:3993-4001 (1991].

The macromolecule can also be a polypeptide such as a cell surface receptor, an enzyme or a structural protein. For example, the second polypeptide region can include a tubulin binding domain of a microtubule associated protein (MAP) or an actin-binding domain of an actin-binding protein. Actin-binding proteins are associated with the plasma membrane and are involved in the interactions between the plasma membrane and the actin cytoskeleton. Actin-binding proteins include, but not limited to, focal adhesion kinase, α-catenin, β-catenin, α-actinin, paxillin, tensin, annexin, ezrin, clathrin-H chain, vinculin, talin, zyxin, profilin, fractinin, cortactin, AFAP-110, p120, connexin 43, supervillin, and cadherins [Annu. Rev. Physiol. 56:169-191 (1994)]; [Proc. Natl. Acad. Sci. U.S.A. 92, 8813-8817, (1995)]; [J. Cell. Biol. 130:67-77, (1995)]; [J. Cell. Biol. 138:181-192, (1997)]; [Cell Motil. *Cytoskeleton* 20:1-6 (1991)]; [Curr. Opin. Cell Biol. 4:834-839, (1992)]; [(Ann. Rev. cell Dev. Biol. 11: 379-416, (1995)]; and U.S. Pat. Nos. 5,985,608, 5,796,819.

The chimeric polypeptide of the present invention can be synthesized using protein synthesis techniques which are well known in the art. Preferably, the chimeric polypeptide of the present invention is synthesized using recombinant techniques utilizing readily available expression vectors.

Thus according to another aspect of the present invention there is provided a polynucleotide encoding the polypeptide of the present invention. An Example of a polynucleotide sequence which encodes one embodiment of the chimeric polypeptide of the present invention is provided in the Examples section which follows.

To express the chimeric polypeptide of the present invention, the polynucleotide is preferably provided in an expression vector suitable for expression in a selected host.

In-vitro expression vectors which can be utilized by the present invention include but are not limited to the pCM-VTNT and pTNT expression vectors available from Promega.

Prokaryotic expression vectors which can be utilized by the present invention include, but are not limited to, the pET or pRSET expression vectors available from Invitrogen.

Yeast expression vectors which can be utilized by the present invention include, but are not limited to, the pNMT expression vectors available from Invitrogen.

Insect expression vectors which can be utilized by the present invention include, but are not limited to pBAC available from Novagen and the pMIB expression vectors available from Invitrogen.

Plant expression vectors which can be utilized by the present invention include, but are not limited to pJD300 and pAL61 available from Promega.

Mammalian expression vectors which can be utilized by the present invention include, but are not limited to, pcDNA3, pcDNA3.1 (+/−), pZeoSV2(+/−), pSecTag2, pDisplay, pEF/myc/cyto, pCMV/myc/cyto, pCR3.1, which are available from Invitrogen, pCI which is available from Promega, pBK- RSV and pBK-CMV which are available from Stratagene, pTRES which is available from Clontech, and their derivatives.

It will be appreciated that any of the above mentioned expression vectors can be further modified to include secretion or targeting signals which can be used to target the expressed chimeric polypeptide of the present invention to a subcellular organelle, a cellular compartment or out of the cell.

Prokaryotic, yeast, insect, plant and mammalian expression vectors constructed to include a polynucleotide encoding the chimeric polypeptide of the present invention can be utilized to transform host cells for the purpose of expressing the chimeric polypeptide therewithin.

Various techniques known to those skilled in the art relating to the transformation of prokaryotic cells are set forth in the following references: Dower, W. J., in Genetic Engineering, Principles and Methods, 12:275-296, Plenum Publishing Corp., 1990; Hanahan et al., Meth. Enzymol., 204:63 (1991).

Various techniques related to the transformation of eukaryotic cells, such as plant cells, are set forth in the following references: Bilang, et al., Gene 100: 247-250 (1991); Scheid et al., Mol. Gen. Genet. 228: 104-112 (1991); Guerche et al., Plant Science 52: 111-116 (1987); Neuhause et al., Theor. Appl. Genet. 75: 30-36 (1987); Klein et al., Nature 327: 70-73 (1987); Howell et al., Science 208: 1265 (1980); Horsch et al., Science 227: 1229-1231 (1985); DeBlock et al., Plant Physiology 91: 694-701 (1989); Methods for Plant Molecular Biology (Weissbach and Weissbach, eds.) Academic Press Inc. (1988); and Methods in Plant Molecular Biology (Schuler and Zielinski, eds.) Academic Press Inc. (1989). See also, U.S. Pat. Nos. 4,945,050; 5,036,006; and 5,100,792, all to Sanford et al. In addition, see U.S. patent application Ser. No. 08/438,666, filed May 10, 1995, and Ser. No. 07/951,715, filed Sep. 25, 1992.

Various techniques related to the transformation of animal cells and insects are set forth in the following references: Wall et al., Transgenic Research 5(1):67-72 (1996); Rexroad et al., Anim. Biotech. 1:1-10 (1990); Hogan et al., Manipulating the Mouse Embryo: a Laboratory Manual. Cold Spring Harbor, N.Y.: Cold Spring Harbor Laboratory Press (1986); Shanahan et al., Mol. Cell. Biol. 9:5473-9 (1989); Alam et al., Transgenic Research 5:87-95 (1996) and references therein; Mitchell, M. F. Amer. J. Obstet. 174:1094-11 (1996); Keller, E. T., The Cancer Gene 3:186-191 (1996); Lo, D., Clin. Immunol. Im. 79:96-104 (1996); Brousseau, M. E., J. Clin. Invest. 97:1844-185 (1996); Kim, C. H., Neurochem. Res. 21:231-237 (1996); Kroshus, T. J., Cd59 Transplantation 61:1513-152 (1996); Cozzi, E., Xenotransplanta 3:128-133 (1996); Dziadek, M., T. Aust. Vet. J. 73:182-187 (1996); Damak, S., Bio-Technology 14:185-188 (1996); Shen, J. H., Faseb. J. 9:1623-1631 (1995); Wall, R. J., Theriogenology 45:57-68 (1996); Simoens, C., P. Hum. Reprod. Upda. 1:523-542 (1995); Wagner, J., Pediat. Nephrol. 10:108-35 U.S.C. .sctn.112, (1996); Duncker et al., Transgenic Research 5:49-55 (1996); Duncker, B. P., Cryobiology 32:521-527 (1995).

As mentioned hereinabove, the chimeric polypeptide of the present invention is constructed for the purpose of highlighting a cell, a cellular component or a macromolecule and as such, it can be utilized in various research and diagnostic methods.

Thus, according to another aspect of the present invention there is provided a method of highlighting a cell compartment, a biological component or macromolecule, in an organism such as a bacterium, a yeast, a fungus, an algae, a plant or an animal.

The method is effected by providing the chimeric polypeptide of the present invention to the organism and exposing the organism to the detectable molecule.

According to embodiments of the present invention, the chimeric polypeptide can either be administered (as a composition) to the organism, or alternatively and preferably it can be expressed within the organism as described above.

Exposing the organism to the detectable molecule can be effected by injection, ingestion, or inhalation (in the case of a mammal), by providing the detectable molecule in the growth medium (in the case of cell cultures) or by irrigation, spraying and the like (in the case of plants).

Exposure of the organism to the detectable molecule highlights the cell compartment, biological component or macromolecule to which the chimeric polypeptide is bound. Such highlighting can be detected using a variety of techniques which depend on the type of detectable molecule utilized.

The highlighted cell compartment, biological component or macromolecule, can be visualized under a microscope in the case of fluorophores chromophores and light emitting molecules. The microscope can be equipped with a light source, such as an ultraviolet light source.

The capacity for sensitive and selective highlighting of specific cell compartments, biological components or macromolecules in situ presents a useful tool for a broad range of applications in biological research and practice.

Thus, the highlighting method of the present invention can be utilized to determine the presence or absence of specific cell compartments, biological components or macromolecules in cells or tissues for the purpose of diagnosis.

For example, by employing a chimeric polypeptide capable of binding a biological component or macromolecule associated with an abnormal phenotype, the present methodology can be utilized to detect cells exhibiting an abnormal phenotype (e.g., cancer cells). Alternatively, by employing a chimeric polypeptide capable of binding a viral component or macromolecule, the present methodology can be utilized to detect virally infected cells. It will be appreciated that in such diagnostic cases it is advantageous to compare the resultant highlighted pattern of the tested cell or organism with that obtained from control cells (e.g., non-infected cells)

Thus, the present invention provides polypeptides and nucleic acid constructs encoding same and methods using the polypeptides or nucleic acid constructs for highlighting cell compartments, biological components or macromolecules. Unlike conventional biological dyes or stains, the present invention is highly site-specific enabling highlighting a particular cellular or subcellular site or even a macromolecule in situ.

One advantage of the present invention is that it can be effected without disrupting cell morphology or function. This is true even in cases where the free detectable molecule utilized is capable of cellular disruption, since capture of the detectable molecule by the chimeric polypeptide may prevent it from altering cellular morphology or function.

In addition, the amount of detectable molecule needed for generating a detectable signal according to the present methodology is minimal since selective capture by the chimeric polypeptide essentially localizes and increases the signal density of the detectable molecule. Such localization also increases the sensitivity of the present methodology since a concentration of signal increases detection capability.

Furthermore, since the expression of the chimeric polypeptide occur continuously, dynamic observations may be facilitated in vivo. The observations can be conducted at any time desired, such as at any particular growth stage or with respect to timing of a treatment, conveniently by administering the detectable molecule and visualizing the highlighted targets.

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Reference is now made to the following example, which together with the above descriptions, illustrates the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes 1-111 Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Preparation and Application of a Nucleic Acid Construct Encoding a Chimeric Polypeptide of the Present Invention The following example illustrates a general procedure for generating and utilizing a nucleic acid construct which is capable of expressing a chimeric polypeptide which includes a first polypeptide region being capable of specifically binding fluorescein molecule (a fluorophore) and a second polypeptide region being capable of specifically binding mouse mitochondrion.

Preparation of a DNA Fragment Encoding Fluorescein Specific scFv

A DNA fragment encoding scFv is isolated and cloned essentially as described by Lorimer et al. [PNAS 93: 14815-14820 (1996)] but with the exception of replacing the antigen used by Lorimer et al (a growth factor receptor) with the detectable molecule fluorescein.

Briefly, mice are immunized with fluorescein-conjugated keyhole limpet hemocyanin in complete Freund's adjuvant. Five days after the final immunization boost, spleens are harvested and poly(A)+ mRNA is purified therefrom using a Ficoll cushion and a FastTrack mRNA isolation kit (Invitrogen). The mRNA is utilized to construct a display library using the recombinant phage system from Pharmacia following the manufacturer's protocol. The final ligation reaction is used to transform *E. coli* TG1 cells (Stratagene) by electroporation. Phages are purified from the TG1 cell culture supernatant and suspended in a solution containing skim milk powder with Tween 20 in PBS containing biotinylated fluorescein. This suspension is mixed end-over-end at room temperature and then added to Dynabeads M-280 streptavidin-coated magnetic beads (Dynal, Great Neck, N.Y.) that are blocked with a solution containing skim milk powder with Tween 20 in PBS. Following incubation, magnetic beads are captured with a magnet and washed with PBS. Beads are resuspended in PBS and used directly to re-infect log phase TG1 cells. The captured phage is analyzed for fluorescein specific scFv by ELISA and the ELISA positive phage is used to prepare phagemids. Finally, the scFv DNA is PCR amplified from a selected phagemids.

Preparation of a DNA Fragment Encoding Mitochondria Binding Peptide

The DNA fragment encoding mouse S-AKAP84 binding peptide is isolated and cloned essentially as described by Chen et al., (1997) [J. Mol. Chem. 272:15247-15257]. Briefly, complementary DNA encoding human S-AKAP84 [Lin et al., (1995) [J. Biol. Chem. 270, 27804-27811] is digested with NdeI and the resulting 1.8-kilobase pair fragment is used as a template to generate a random-primed, $^{32}$P-labeled probe. This probe is used to screen a mouse testis cDNA library in bacteriophage λgt11 (Clonetech) Positive recombinant phage clones are plaque purified and cDNAs (0.9-2.9 kilobase pair) are subcloned in plasmids pGEM7Z (Promega) and pBluescript (Stratagene). A selected fragment of S-AKAP84 cDNA is amplified by PCR.

Generating the Nucleic Acid Construct Encoding the Chimeric Polypeptide

Figure 1:
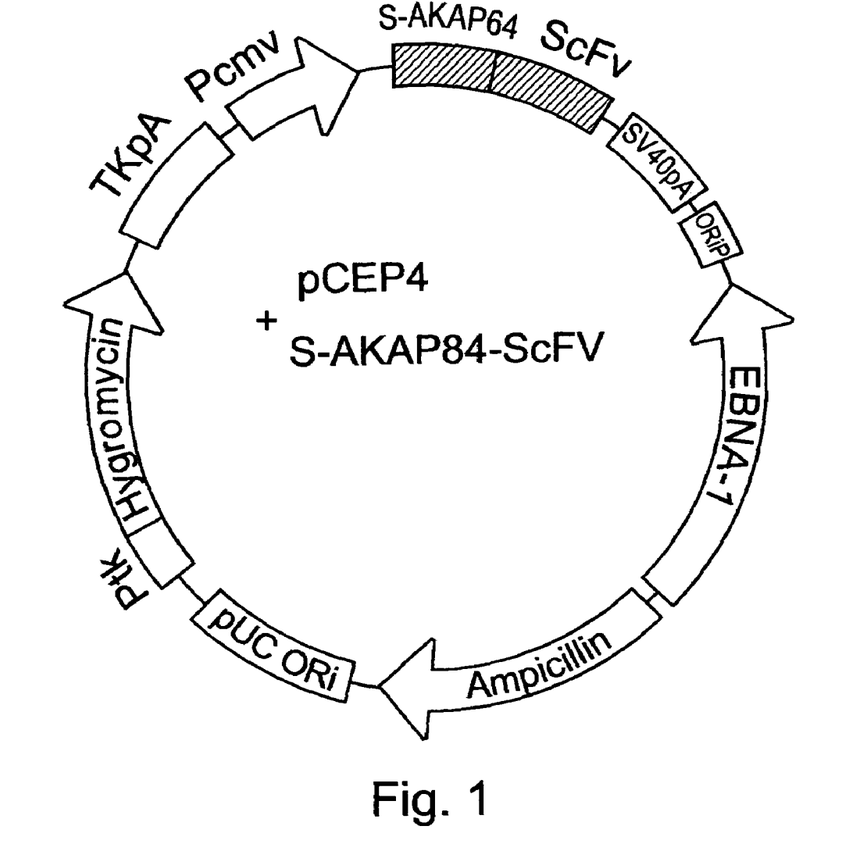
FIG. 1 is a map of one embodiment of the nucleic acid construct of the present invention.
Figure 2:
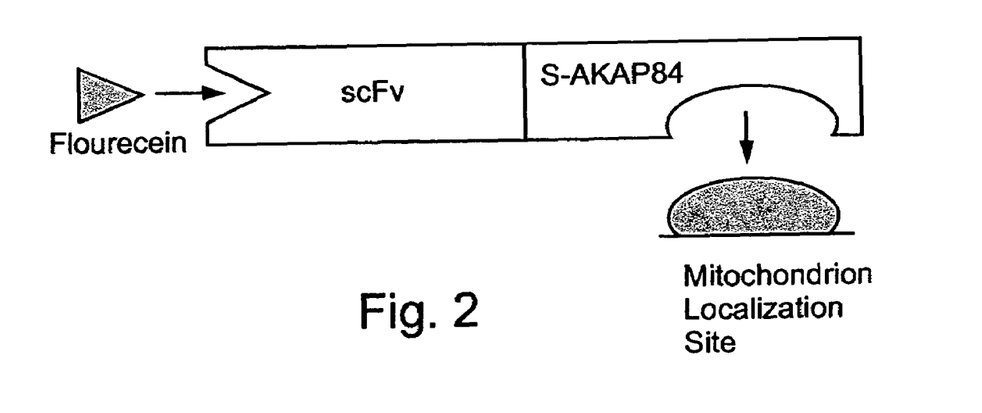
FIG. 2 is a schematic diagram of the chimeric polypeptide expressed from the nucleic acid construct of FIG. 1.

The DNA fragment encoding fluorescein-specific scFv is fused in frame to the DNA fragment encoding S-AKAP84. the fusion product is PCR amplified and the PCR product is cleaved with HindIII and XhoII and cloned into the expression plasmid pCEP4 (Invitrogen) which is cleaved with the same enzymes. This places the chimeric DNA downstream of the cytomegalovirus promoter and upstream of the polyadenylation signal. pCEP4 also contains a bacterial hygromycin B phosphotransferase gene under regulation of a strong viral thymidine kinase promoter. The isolated construct (FIG. 1) is sequenced to verify sequence integrity. The polypeptide expressed from the nucleic acid construct is illustrated in FIG. 2.

Transfection of Cells with the Nucleic Acid Construct, Administration of the Fluorophore and Visualization Human embryonic kidney cells (HEK293) are grown and transfected as described by Ndubuka et al., (1993) [J. Biol. Chem. 268:7621-7624]. Transfected HEK293 cells are immersed in a fluorescein solution then thoroughly washed. Fluorescence signals and highlighted mitochondria are observed using a DeltaVision digital microscopy system (Applied Precision, USA)

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of detecting a compartment of a cell or a macromolecule of the cell, the method comprising:
   (a) expressing a polynucleotide encoding a chimeric polypeptide in the cell, said chimeric polypeptide including:
      (i) a first polypeptide region being capable of specifically binding at least one detectable molecule, said first polypeptide region comprising a single chain Fv; and
      (ii) a second polypeptide region being capable of specifically binding the macromolecule of the cell; or targeting into a specific cell compartment, said second polypeptide region comprising S-AKAP84;
   (b) exposing the cell to said detectable molecule under conditions suitable for binding of said detectable molecule to said first polypeptide region; and
   (c) analyzing a presence of said detectable molecule in the compartment of the cell, or in association with said macromolecule of the cell, thereby detecting the compartment of the cell or macromolecule of the cell.

2. The method of claim 1, wherein the cell is selected from the group consisting of a bacterium cell, a protozoa cell, a fungus cell, a yeast cell, an algae cell, a plant cell and an animal cell.

3. The method of claim 1, wherein step (a) is effected by transfecting a nucleic acid construct encoding said chimeric polypetide into the cell.

4. The method of claim 1, wherein step (b) is effected by contacting said cell and said detectable molecule in a culture medium.

5. The method of claim 1, further comprising a step of visualizing said detectable molecule.

6. The method of claim 5, wherein said visualizing is effected using a microscope.

7. The method of claim 6, wherein said microscope is equipped with a light source.

8. A method of detecting a compartment of a cell comprising:
   (a) expressing a polynucleotide encoding a chimeric polypeptide in the cell, said chimeric polypeptide including:
      (i) a first polypeptide region being capable of specifically binding at least one detectable molecule; and
      (ii) a second polypeptide region being capable of targeting into a specific cell compartment; and
   (b) exposing the cell to said detectable molecule under conditions suitable for binding of said detectable molecule to said first polypeptide region; and
   (c) analyzing a presence of said detectable molecule in the compartment of the cell, thereby detecting the compartment of the cell.

9. The method of claim 8, wherein the cell is selected from the group consisting of a bacterium cell, a protozoa cell, a fungus cell, a yeast cell, an algae cell, a plant cell and an animal cell.

10. The method of claim 8, wherein step (a) is effected by transfecting a nucleic acid construct encoding said chimeric polypetide into the cell.

11. The method of claim 8, wherein step (b) is effected by contacting said cell and said detectable molecule in a culture medium.

12. The method of claim 8, further comprising a step of visualizing said detectable molecule.

13. The method of claim 12, wherein said visualizing is effected using a microscope.

14. The method of claim 13, wherein said microscope is equipped with a light source.

15. The method of claim 8, wherein the second polypeptide region comprises a domain selected from the group consisting of a cell adhesion molecule binding domain, a membrane anchor protein domain, a human SDH Q-reductase domain, a growth factor receptor domain, a receptor binding domain, a protein kinase AII domain, a cellulose binding domain, a lipid binding domain, a polynucleotide binding domain, a tubulin binding domain and an actin binding domain.

16. A method of detecting a compartment of a cell or a macromolecule of the cell, the method comprising:
(a) expressing a polynucleotide encoding a chimeric polypeptide in the cell, said chimeric polypeptide including:
  (i) a first polypeptide region being capable of specifically binding at least one detectable molecule; and
  (ii) a second polypeptide region being capable of specifically binding the macromolecule of the cell; or targeting into a specific cell compartment, said second polypeptide region comprising a domain selected from the group consisting of a cell adhesion molecule binding domain, a membrane anchor protein domain, a human SDH Q-reductase domain, a growth factor receptor domain, a receptor binding domain, a protein kinase AII domain, a cellulose binding domain, a lipid binding domain, a polynucleotide binding domain, a tubulin binding domain and an actin binding domain;
(b) exposing the cell to said detectable molecule under conditions suitable for binding of said detectable molecule to said first polypeptide region; and
(c) analyzing a presence of said detectable molecule in the compartment of the cell, or in association with said macromolecule of the cell, thereby detecting the compartment of the cell or macromolecule of the cell.

* * * * *